United States Patent [19]
Davies et al.

[11] Patent Number: 5,770,392
[45] Date of Patent: Jun. 23, 1998

[54] METHOD AND COMPOSITION FOR IDENTIFYING INHIBITORS OF EUKARYOTIC CELL PROCESSES

[75] Inventors: Julian E. Davies, Vancouver; Barbara Waters, Delta, both of Canada

[73] Assignee: TerraGen Diversity Inc., Vancouver, Canada

[21] Appl. No.: 733,686

[22] Filed: Oct. 17, 1996

[51] Int. Cl.$^6$ .............................. C12Q 1/48; C12Q 1/34; C12Q 1/37; C12N 1/00

[52] U.S. Cl. ................................. 435/15; 435/18; 435/4; 435/17; 435/23; 435/24; 435/886; 435/897; 435/240.1

[58] Field of Search .................................. 435/15, 18, 4, 435/17, 886, 897, 240.1, 23, 24

[56] References Cited

PUBLICATIONS

Altschul, S. F., Gish, W., Miller, W., Myers, E. and Lipman, D. 1990 Basic local alignment tool. J. Mol. Biol. 215:403–410.

Av–Gay, Y. and Davies, J. 1997 Components of eukaryotic–like protein signaling pathways in *Mycobacterium tuberculosis*. Microbial & Comparative Genomics 2:63–73.

Georgiou, G, Lin, S–C.,and Sharma, M. 1992 Surface–active compounds from microorganisms. Biotechnology 10:60–65.

Gerrard, J., Lloyd, R., Barsby, T., Haden, P., Kelly, M and Anderson, R. 1997 Massetolides A–H, antimycobacterial cyclic depsipeptides produced by two Pseudomonads isolated from marine habitats. J. Nat. Prod. 60:223–229.

Huneck, S. and Yoshimura, I. 1996 Identification of lichen substances. Springer–Verlag, Berlin.

Lane, D. 1991 16S/23S rRNA sequencing, pp. 115–175 In Stackebrandt, E. and Goodfellow, M (ed.), Nucleic acid techniques in bacterial systematics, John Wiley and Sons, Chichester.

Lauterwein, M., Oethinger, M., Belsner, K., Peters, T. and Marre, R. 1995 In vitro activities of the lichen secondary metabolites vulpinic acid, (+)–usnic acid and (–)–usnic acid against aerobic and anaerobic microorganisms. Antimicrobial Agents and Chemotherapy 39:2541–2543.

Stachelhaus, T., Schneider, A. and Marahiel, M. 1996 Engineered biosynthesis of peptide antibiotics. Biochemical Pharmacology 52:177–186.

Toraya, T., Maoka, T., Tsuji, H. and Kobayashi, M. 1995 Purification and structural determination of an inhibitor of starfish oocyte maturation from a Bacillus species. Applied and Environmental Micro. 5:1799–1804.

Natsume et al. Calcium Signal Modulators Inhibit Aerila Mycelium Formation in *Streptomyces alboniger, J. Antibiotics* 45: 1026–1028 (1992). Month not available. Please print.

Hong et al., "Effects of protein kinase inhibitors on in vitroprotein phosphorylation and cellular differentiation of *Streptomyces griseus*", *Mol. Gen. Genetics* 236: 347–354 (1993). Month not available. Please print.

Kennelly et al., "Fancy Meeting You Here! A Fresh Look at 'Prokaryotic' Protein Phosphorylation", *J. Bacteriol.* 178: 4759–4764 (1996). Month not available. Please print.

Karin et al., "Transcriptional control by protein phosphorylation: signal transmission from cell surface to nucleus", *Current Biology* 5: 747–757 (1995). Month not available. Please print.

Ray, L.B., "Signals and Communication," *Science* 268: 183 (1995). Month not available. Please print.

Casey, P.J., "Protein Lipidation in Cell Signaling", *Science* 268: 224–225 (1995). Month not available. Please print.

Burbulys et al., "Initiation of Sporulation in B. subtilis Is controlled by a Multicomponent Phosphrelay" *Cell* 64: 545–552 (1991). Month not available. Please print.

Stock et al., "Protein Phosphorylation and Regulation of Adaptive Responses in Bacteria", *Microbiol. Reviews* 53: 450–490 (1989). Month not available. Please print.

South et al., "Tyrosine Kinase sctivity in *Pseudomonas aeruginosa*", *Molecular Microbiol.* 12: 903–910 (1994). Month not available. Please print.

Chow et al., "Protein tyrosine phosphorylation in *Mycobacterijm tuberculosis*", *FEMS Microbiol. Lett.* 124: 203–208 (1990). Month not available. Please print.

Li et al., "Cloning, Purification and Properties of a Phosphotyrosine Protein Phosphatase from *Streptomyces coelicolor* A3(2)", *J. Bacteriol.* 178: 136–142 (1996). Month not available. Please print.

Frasch et al., "Tyrosine Kinase in *Myxococcus xanthus*, a Multicellular Prokaryote", preprint of article submitted to *J. Bacteriol* (1996). Month not available. Please print.

Zhang, C–C., "Bacterial Signalling Involving Eukaryotic–type Protein Kinases" *Molecular Microbiol.* 20: 91–5 (1996). Month not available. Please print.

(List continued on next page.)

*Primary Examiner*—Louise N. Leary
*Attorney, Agent, or Firm*—Oppedahl & Larson

[57] ABSTRACT

Materials can be assayed for activity as an inhibitor of post-translational protein phosphorylation by adding the material to a growing culture of a prokaryotic organism such as a streptomycete; allowing the culture to grow for a period of time in the presence of the material; and observing the culture for altered development relative to development of the prokaryotic organism grown in the absence of the material. Observation of altered development is indicative that the material has activity as an inhibitor of post-translational protein phosphorylation. In particular, the material to be tested can be added to a growing culture of the prokaryotic organism by placing a carrier disk bearing the material on a freshly seeded plate. Inhibition of the development of aerial mycelia and spore formation is an indicator that the material has activity as an inhibitor of post-translational protein phosphorylation.

15 Claims, No Drawings

OTHER PUBLICATIONS

Zhang et al., "Identification of a Putative Eukaryotic–Like Protein Kinase Family in the Developmental Bacterium *Myxococcus xanthus*" *J. Bacteriol.* 174: 5450–5453 (1992). Month not available. Please print.

Meydan et al., "Inhibition of acute lymphoblastic leukaemia by a Jak–2 inhibitor" *Nature* 379: 645–648 (1996). Month not available. Please print.

"Leukemia–fighting drug found to work in mice", *Vancouver Sun*, Feb. 15, 1996, p. A11. Month not available. Please print.

Clark et al., "Integrins and Signal Transduction: The Road Taken", *Science* 268: 233–234 (1995). Month not available. Please print.

Machly–Rosen, D., "Localization of Protein Kinases by Anchoring Proteins: A Theme in Signal Transduction", *Science* 268: (1995). Month not available. Please print.

De Franco et al., "Tyrosine Phosphatases and Antibody Response" *Science* 268: 263–264 (1995). Month not available. Please print.

5,770,392

METHOD AND COMPOSITION FOR IDENTIFYING INHIBITORS OF EUKARYOTIC CELL PROCESSES

BACKGROUND OF THE INVENTION

This application relates to a method and kit for assaying materials for activity as inhibitors of kinase and phosphatase enzymes.

Kinase and phosphatase enzymes play important roles in the regulation of both eukaryotic and prokaryotic cells. For example, in eukaryotic cells, the control of proliferation and differentiation is achieved by multiple signal transduction pathways that are regulated by the coordinated action of protein kinases and phosphatases. Prokaryotic cells also rely on protein phosphorylation cascades for regulation of cellular activities. These kinases, and their associated response regulators are involved in adaptive responses such as nitrogen fixation, chemotaxis in enteric bacteria and regulation of sporulation in Bacillus species.

Kinase activity in eukaryotes can be classified as one of three types: those enzymes which phosphorylate tyrosine residues; those which are specific for serine or threonine residues; and those which have dual specificity for both tyrosine and serine/threonine residues. Because of the importance of these enzymes in eukaryotic regulatory processes, it would be highly desirable to be able to inhibit kinases of the various classes selectively to assist in the elucidation of kinase and phosphatase mediated pathways, particularly those that may be of medical significance. In addition, selective kinase or phosphatase inhibitors have potential uses as therapeutics. For example, it has been reported that a tyrosine kinase blocker designated AG-940 specifically inhibits the Jak-2 protein tyrosine kinase which is deregulated and constitutively activated in the leukemic cells of acute lymphoblastic leukemia (ALL) patients. Meydan, et al. "Inhibition of acute lymphoblastic leukaemia by a Jak-2 inhibitor", *Nature* 379: 645–648 (1996). This inhibition induced changes in cells consistent with entry into apoptosis when tested in vitro. Further, the intravenous administration of the inhibitor into mice previously injected with ALL cells has been shown to be effective to eradicate the ALL cells from the marrow.

Notwithstanding the potential uses of kinase and phosphatase inhibitors, the number of known and characterized inhibitors is quite small. Staurosporine and K-252a are known to act as generalized kinase inhibitors, while herbimicin and radicol specifically inhibit tyrosine kinases, albeit with fairly low effectiveness. There are no known specific inhibitors for the MAP kinase family, an important group of enzymes thought to be central in the transmission of a wide variety of signals received at the cellular membrane to the transcriptional and replication machinery of the nucleus.

To facilitate the identification of new kinase and phosphatase inhibitors, it would be very advantageous to have a simple, visually-scorable assay methodology for inhibition activity. It is an object of the present invention to provide such a method and a kit useful in practicing the method.

It is a further object of the invention to provide a microbial strain which is particularly suited for use in the present invention.

SUMMARY OF THE INVENTION

In accordance with the present invention, a material can be assayed for activity as an inhibitor of post-translational protein phosphorylation by adding the material to a growing culture of a prokaryotic organism such as a streptomycete;
 allowing the culture to grow for a period of time in the presence of the material; and
 observing the culture for altered development relative to development of the prokaryotic organism grown in the absence of the material. Observation of altered development is indicative that the material has activity as an inhibitor of post-translational protein phosphorylation. In particular, the material to be tested can be added to a growing culture of the prokaryotic organism by placing a carrier disk bearing the material on a freshly seeded plate. Inhibition of the development of aerial mycelia and spore formation is an indicator that the material has activity as an inhibitor of post-translational protein phosphorylation.

DETAILED DESCRIPTION OF THE INVENTION

Although eukaryotic and prokaryotic protein kinases generally have different substrate specificities, it has been observed that in some prokaryotic organisms eukaryote-like kinase and phosphatase activities may complement the two component systems typical of bacteria. In particular, *streptomycetes*, (Waters et al., "Protein tyrosine phosphorylation in *streptomycetes*", FEMS Microbiology Letter 120: 187–190 (1994); Li et al., "Cloning purification and properties of a phosphotyrosine protein phosphatase from *Streptomyces coelicolor* A3(2)", *J. Bact.* 178: 136–142 (1996)); *Myxococcus xanthus* (Zhang et al., "Identification of a putative eukaryotic-like protein kinase family in the developmental bacterium *Myxococcus xanthus*", *J. Bact.* 174: 5450–5453 9192); and *cyanobacterial* species. (Zhang, C—C, "Bacterial signaling involving eukaryotic-type protein kinases", *Molec. Microbiol.* 20: 9–15 (1996)). The present invention takes advantage of this property of certain microbes to provide an assay for screening materials for activity as inhibitors of eukaryotic post-translational protein phosphorylation.

The present invention is applicable to the evaluation of any type of material for activity as an inhibitors of eukaryotic post-translational protein phosphorylation. Thus, the method of the invention can be employed to screen purified compounds. A preferred use of the invention, however, is for screening cell-free preparations derived from cultures of uncharacterized or poorly characterized microorganisms to identify those which produce natural product inhibitors of protein phosphorylation.

In accordance with the present invention, the first step in assay method is adding the material to be evaluated to a growing culture of a prokaryotic test organism which possesses enzyme activity effective to phosphorylate tyrosine, serine or threonine residues within a protein. Preferably, the organism will possess both tyrosine and serine/threonine specific enzymes.

Suitable prokaryotic test organisms for use in the assay of the invention are *streptomycetes*, particularly strains of *Streptomyces griseus,* and a number of wild stains (e.g., strains designated as WEC93-17A, WEC188-31C, WEC362-68A and WEC403-73F) demonstrated to be distinct by sequencing of the 16S rDNA. A particularly preferred prokaryotic organism is a wild strain of *Streptomyces* isolated from soil and designated *Streptomyces* WEC478-85E (hereinafter strain 85E). This strain has been deposited with the American Type Culture Collection in accordance with the provisions of the Budapest treaty and has been assigned Accession Number ATCC 55824.

The material to be tested can be applied to a filter paper disk and then placed on a plate which has been freshly seeded with the prokaryotic test organism. The prokaryotic test organism is then allowed to grow in the presence of the filter paper disk for a period of 24 to 36 hours, after which the organism is evaluated for altered development in the zone around the disk. The effects observed may include overall growth inhibition, but at least in the case of *streptomycetes*, an observation of an inhibition of the formation of aerial mycelia and spores, without inhibition of the growth of vegetative mycelia is particularly indicative of the presence of an inhibitor of post-translational phosphorylation.

Depending on the specific test organism used, the growth medium employed may need to be a minimal media or a rich medium. This is the case because it appears that the metabolic pathways facilitating growth on minimal media are different from those operational during growth on rich media, and it may be the case that different kinases and phosphatases may be regulating development and metabolism under different growth conditions. It may also be advantageous to test materials using both a rich and a minimal medium.

In the case of *Streptomyces* 85E, the method of the invention is preferably performed using a minimal medium such as ISP4, an inorganic salts/starch agar available from Difco, because this strain sporulates readily when grown on this medium. This facile sporulation makes it easy to make a visual evaluation for differences in spore formation, leading to an easily scored assay. Strains (such as 17A and 31C) which sporulate on rich medium, for example tryptic soy medium, can also be used in the assay of the invention.

Materials which are identified as being or containing potential inhibitors of eukarybtic post-translational phosphorylation based upon their ability to effect the growth of the prokaryotic test organism may be further tested using one or more class specific assays to confirm and characterize the type of enzymes inhibited. For example, the materials may be tested in individual assays for inhibition of MAP kinase activity, tyrosine kinase activity, e.g. src activity, or serine/threonine kinase activity, e.g., cdc2 activity. Using the method of the invention in combination with such assays, we have identified several kinase-specific inhibitors including a MAP kinase inhibitor, src kinase and cdc2 kinase.

Although the main application for the present invention is in screening for inhibitors of post-translational phosphorylation, the bacterial assay system of the invention is in reality effective as a screening tool for inhibition of signaling pathways in eukaryotes generally. Thus, in addition to kinase and phosphatase inhibitors, the assay of the invention is useful for screening for inhibitors of cell-cycle development, inhibitors of apoptosis, inhibitors of signal mediation via calcium, and inhibitors of other eukaryotic processes that involve post-translational modification.

The assay offers a simple and effective pre-screening tool which is easily scored, and which lends itself to automated, high-throughput screening. Further, materials selected for further evaluation as a result of the assay are already known to effective in the cell, unlike activities based on in vitro assay systems. Most importantly, the assay system is not affected by compounds in the materials being tested that are cytotoxic to mammalian cells, thus interfering with assays using mammalian cells, and avoids problems with protease contaminants that do not interfere with microbial morphological assays but are a serious problem with animal cell and isolated receptor assays.

The invention will now be further described and illustrated by way of the following, non-limiting examples.

EXAMPLE 1

A screening assay was run on a total of 1000 soil sample isolates using *Streptomyces* 85E as the prokaryotic test organism. Each isolate was grown in tryptic soy broth (Difco) for a period of 2–3 days. A cell-free culture supernatant was then collected by centrifugation at 17,000×g for 10 minutes. 30 $\mu$l of this supernatant was dispensed onto a 12 mm diameter filter paper disk. The disks were then placed on plates prepared from ISP4 minimal medium and freshly seeded with *Streptomyces* 85E. The plates were incubated for 24 to 36 hours at 30° C. in a standard incubator cabinet. During this time, the cultures were observed for differences in growth and/or development in the areas surrounding the disk.

Fifty-two of the 1000 isolates, including species of *Streptomyces, Bacillus* and *Pseudomonas*, were found to produce a supernatant which affects the sporulation of the indicator strain *Streptomyces* 85E.

In a follow-up experiment, this test was repeated using 10-fold and 100-fold dilutions of the original supernatant for three of the stronger inhibitors. Sporulation of the indicator strain *Streptomyces* 85E was seen to be reduced with the 10-fold dilution but could not be detected with the 100-fold dilution.

EXAMPLE 2

Thirty seven of the supernatants found to inhibit sporulation of *Streptomyces* 85E were tested for their ability to inhibit sporulation in *Streptomyces griseus* ATCC No. 23345 using the same procedure described in Example 1. Sixteen of the supernatants were found to inhibit sporulation of this strain. Thus, *Streptomyces griseus* ATCC No. 23345 can be used in the assay of the invention, although it is less sensitive than *Streptomyces* 85E.

EXAMPLE 3

The fifty two supernatants found to inhibit sporulation of Streptomyces 85E were tested for their ability to inhibit growth of a gram positive bacterium (*S. aureus* RN450), a gram negative bacterium (*E. coli* strain DB10), and a yeast species (*S. cerevisiae* strain RC1-707). Most did not affect growth of the bacterial species. A few had anti-fungal activity reflected by inhibition of the yeast. Thus, the selection criteria provided by *Streptomyces* 85E cannot be generally duplicated using other common organisms.

EXAMPLE 4

Isolate 60A (believed to be a *Bacillus* species related by 16S rDNA sequence analysis to *Bacillus licheniformis*) which tested positive in Example 1 was grown in tryptic soy broth (Difco) for 24 to 48 hours. A crude cell-free supernatant was recovered by centrifugation at 17,000×g for 10 minutes. This crude supernatant was sterilized by passage though a 0.2 micron filter and then used for further tests to evaluate inhibition of MAP kinase.

Tests for MAP kinase inhibition were performed using standard reagents and protocols equivalent to those supplied by from Upstate Biotechnology. 30 ul reactions mixtures were prepared containing MAPK enzyme, myelin basic protein as substrate and 5 ul of the crude supernatant. The reaction mixtures were incubated for 10 minutes at 30° C. with $\gamma$–$^{32}$P-ATP, and the radioactivity incorporated in the protein was determined by scintillation counting. In duplicate experiments, the activity in the sample containing the crude supernatant was found to be only 3.8% and 6.25% of the activity of a control. Thus, isolate 60A produces an effective inhibitor of MAP kinase.

EXAMPLE 5

The experiment of Example 4 was repeated on supernatants from eleven additional isolates that were positive in the sporulation inhibition assay. Of these eleven supernatants, a total of five were effective to inhibit MAP Kinase. As shown in Table 1, this activity persisted even when the crude preparation was diluted 10-fold.

TABLE 1

| Isolate | % Activity - Crude Supernatant | % Activity - 10-fold Dilution |
|---|---|---|
| Control | 100 | |
| 60A (putative Bucillus) | 2 | 14.5 |
| 152-O (putative Bacillus) | 2 | 37.5 |
| 11C (putative Pseudomonas) | 42 | 73 |

EXAMPLE 6

To confirm that the inhibition in the MAP kinase assay was caused by a low molecular weight material and was not an artifact arising from the presence of a protease or ATPase, the crude supernatants were filtered through a filter unit with a molecular weight cut-off of 10,000 daltons. The filtered supernatant was then tested for its ability to inhibit MAP kinase. Supernatant from an isolate (31C) which showed no activity in the sporulation test of Example 1 was also run as an additional control. The results are shown in Table 2. As can be seen, the inhibitory activity remained in the filtrates. The supernatant from isolate 31C did not inhibit the MAP kinase activity.

TABLE 2

| Sample | % Activity, Crude | % Activity, Filtered |
|---|---|---|
| Control | 100 | |
| 60A | 62 | 83 |
| 152-O | 64 | 74 |
| 11C | 58 | 89 |
| 31C | 97 | n.d. |

EXAMPLE 7

The crude and filtered supernatant from isolate 60A was tested for its ability to inhibit the tyrosine kinase, src, using commercially available reagents and protocols. The activity observed for the crude supernatant was 61% percent of the control while that for the filtrate was 67% of the control. Thus, the supernatant from 60A also inhibited tyrosine kinase.

EXAMPLE 8

The crude supernatant from isolate 60A was tested for its ability to inhibit the serine/threonine kinase, cdc2, using reagents and protocols such as those supplied by Upstate Biotechnology. The activity observed for the crude supernatant was 99% percent of the control. Thus, the supernatant from 60A does not inhibit serine/threonine kinase.

EXAMPLE 9

Marked inhibition of four additional wild strains (17A, 31C, 68A and 73F) was observed in tests using a number of the supernatants found to inhibit sporulation of strain 85E. 16S rDNA sequence data demonstrates a 40 base pair region in which considerable sequence variability has been noted. Comparison of the these sequences with those in GenBank suggest that these strains are probably four different species of *Streptomyces* and that all are different from Strain 85E and from *Streptomyces griseus*.

We claim:

1. A method for testing a material to determine if the material possesses activity as an inhibitor of eukaryotic post-translational protein modification, calcium signal modulation, cell-cycle development or apoptosis comprising
    adding the material to a growing culture of a *prokaryotic* organism which possesses enzyme activity effective to phosphorylate tyrosine, serine or threonine residues within a protein;
    allowing the culture to grow for a period of time sufficient for visually detectable growth to occur in the presence of the material; and
    observing the culture for altered development relative to development of the prokaryotic organism grown in the absence of the material, wherein altered development is indicative that the material has activity as an inhibitor of post-translational protein phosphorylation, calcium signal modulation, cell-cycle development or apoptosis.

2. The method according to claim 1, wherein the material is added to a growing culture of the prokaryotic organism by placing a carrier disk bearing the material on a freshly seeded plate.

3. The method according to claim 1, wherein the prokaryotic organism is a streptomycete.

4. The method according to claim 3, wherein the wherein the culture is observed for the inhibited development of aerial mycelia and spore formation as an indicator that the material has activity as an inhibitor of post-translational protein phosphorylation.

5. The method according to claim 3, wherein the streptomycete is a strain of *Streptomyces griseus*.

6. The method according to claim 3, wherein the streptomycete is *Streptomyces* 85E (ATCC No. 55824).

7. A method for testing a material to determine if the material possesses activity as an inhibitor of eukaryotic enzymes comprising
    adding the material to a growing culture of a prokaryotic organism which possesses enzyme activity effective to phosphorylate tyrosine, serine or threonine residues within a protein;
    allowing the culture to grow for a period of time sufficient for visually detectable growth to occur in the presence of the material; and
    observing the culture for altered development relative to development of the prokaryotic organism grown in the absence of the material, wherein altered development is indicative that the material has activity as an enzyme inhibitor.

8. The method according to claim 7, wherein the material is added to a growing culture of the prokaryotic organism by placing a carrier disk bearing the material on a freshly seeded plate.

9. The method according to claim 7, wherein the prokaryotic organism is a streptomycete.

10. The method according to claim 9, wherein the culture is observed for the inhibited development of aerial mycelia and spore formation as an indicator that the material has activity as an inhibitor of post-translational protein phosphorylation.

11. The method according to claim 9, wherein the streptomycete is a strain of *Streptomyces griseus*.

12. The method according to claim 9, wherein the streptomycete is *Streptomyces* 85E (ATCC No. 55824).

13. A substantially pure culture of Streptomyces 85E (ATCC No. 55824).

14. The method of claim 1, wherein the material tested is a supernatant from a microbial culture.

15. The method of claim 7, wherein the material tested is a supernatant from a microbial culture.

* * * * *